(12) United States Patent
Ferrer

(10) Patent No.: US 11,040,162 B2
(45) Date of Patent: Jun. 22, 2021

(54) SYSTEMS AND METHODS INVOLVING TRACHEOSTOMY VALVE ASSEMBLIES

(71) Applicant: Gustavo Ferrer, Southwest Ranches, FL (US)

(72) Inventor: Gustavo Ferrer, Southwest Ranches, FL (US)

(*) Notice: Subject to any disclaimer, the term of this patent is extended or adjusted under 35 U.S.C. 154(b) by 467 days.

(21) Appl. No.: 16/124,774

(22) Filed: Sep. 7, 2018

(65) Prior Publication Data

US 2019/0070376 A1 Mar. 7, 2019

Related U.S. Application Data

(60) Provisional application No. 62/555,272, filed on Sep. 7, 2017.

(51) Int. Cl.
*A61M 16/04* (2006.01)
*A61M 16/20* (2006.01)
(Continued)

(52) U.S. Cl.
CPC .... *A61M 16/0468* (2013.01); *A61M 16/0402* (2014.02); *A61M 16/0816* (2013.01);
(Continued)

(58) Field of Classification Search
CPC ............ A61M 16/0468; A61M 16/208; A61M 16/201; A61M 16/205; A61M 16/0402;
(Continued)

(56) References Cited

U.S. PATENT DOCUMENTS 6,921,417 B2 * 7/2005 Persson ..................... A61F 2/20
623/9
9,173,669 B2 11/2015 Mathis et al.
(Continued)

OTHER PUBLICATIONS

Passy-Muir Tracheostomy and Ventilator Speaking Valve Resource Guide, Mar. 2003.

*Primary Examiner* — Margaret M Luarca
(74) *Attorney, Agent, or Firm* — Albert Bordas, P.A.

(57) ABSTRACT

A representative method includes: providing a tracheostomy valve assembly having a housing and a diaphragm, the housing defining an interior airflow path, the housing having an exterior surface, a distal opening extending from the exterior surface to the interior flow path and a proximal opening, the distal opening and the proximal opening communicating with the interior airflow path, the diaphragm being disposed within the housing along the interior airflow path, the diaphragm being biased to a closed position to prevent air from passing the diaphragm along the interior airflow path, the diaphragm being configured to selectively move to an open position to enable air to be drawn into the distal opening, passed the diaphragm, and out of the proximal opening in an inhaling direction in response to a proximal side of the diaphragm being exposed to a predetermined negative air pressure applied at the diaphragm as a suction force; and urging the diaphragm away from the closed position with an actuation surface, movably coupled to the housing, to adjust airflow restriction through the tracheostomy valve assembly.

18 Claims, 9 Drawing Sheets

(51) Int. Cl.
*A61M 16/08* (2006.01)
*A61M 16/10* (2006.01)
*A61M 15/00* (2006.01)

(52) U.S. Cl.
CPC .......... *A61M 16/20* (2013.01); *A61M 16/201* (2014.02); *A61M 16/208* (2013.01); *A61M 15/002* (2014.02); *A61M 16/106* (2014.02); *A61M 2205/3334* (2013.01); *A61M 2205/583* (2013.01)

(58) Field of Classification Search
CPC .. A61M 16/20; A61M 39/10; A61M 39/1055; A61F 2/203
See application file for complete search history.

(56) References Cited

U.S. PATENT DOCUMENTS

2012/0097170 A1* 4/2012 Dawson ............ A61M 16/0468
128/207.16
2015/0083119 A1* 3/2015 Persson ............ A61M 16/0468
128/201.13

* cited by examiner

SYSTEMS AND METHODS INVOLVING TRACHEOSTOMY VALVE ASSEMBLIES

CROSS REFERENCE TO RELATED APPLICATION

This utility application claims the benefit of and priority to U.S. Provisional Application 62/555,272, filed on 7 Sep. 2017, which is incorporated by reference herein in its entirety.

BACKGROUND

Technical Field

The disclosure generally relates to tracheostomy valves and, in particular, to systems and methods that are configured to accommodate adjustable airflow rates.

Description of the Related Art

Patients with tracheostomies are often fitted with tracheostomy valves that incorporate diaphragms for permitting the bi-directional flow of air through the valves. Unfortunately, however, most patients are initially unable to tolerate these conventional valves, with many describing the sensation of suffocation. The current standard of care for such patients is to perform daily trails directed and coached by respiratory therapists and/or nurses until the patients can tolerate the valves for a requisite period of time. It is, therefore, desirable to provide improvements in order to address these perceived shortcomings.

SUMMARY

Systems and methods involving tracheostomy valve assemblies are provided. An example embodiment, among various others, is a system comprising: an adjustable-flow tracheostomy valve assembly having a housing, a diaphragm, and a flow-adjustment component; the housing defining an interior airflow path, the housing having an exterior surface, a distal aperture defining a distal opening extending from the exterior surface to the interior airflow path, and a proximal aperture defining a proximal opening, the distal opening and the proximal opening communicating with the interior airflow path; the diaphragm being disposed within the housing along the interior airflow path between the distal opening and the proximal opening, the diaphragm being biased to a closed position to prevent air from passing the diaphragm along the interior airflow path, the diaphragm being configured to selectively move to an open position to enable air to be drawn into the distal opening, passed the diaphragm, and out of the proximal opening in an inhaling direction in response to a proximal side of the diaphragm being exposed to a predetermined negative air pressure applied at the diaphragm as a suction force; the flow-adjustment component having a wall portion with an inner surface configured to conform to the exterior surface of the housing, the wall portion further having a flow-adjustment aperture defining a flow-adjustment opening, the wall portion being movable relative to the housing between an open position, at which the wall portion does not obstruct airflow through the distal opening, and a closed position, at which the wall portion prevents air from passing through the flow-adjustment opening and into the distal opening.

In some embodiments, the wall portion is configured to move with an entirety of the flow-adjustment component.

In some embodiments, the flow-adjustment component has a sidewall, an inner surface of which defines a receptacle, which is configured to receive therein a distal end of the housing such that the distal opening is positioned within the receptacle.

In some embodiments, the wall portion is a portion of the sidewall.

In some embodiments, the sidewall of the flow-adjustment component is cylindrical.

In some embodiments, the wall portion is rotatable relative to the housing.

In some embodiments, the flow-adjustment component and the housing are configured to exhibit a first indexed position between the open position and the closed position.

In some embodiments, engagement between a mating feature disposed on an inner surface of the flow-adjustment component and a corresponding mating feature of the exterior surface of the housing set the first indexed position.

In some embodiments, of the mating feature and the corresponding mating feature, one is a protruding rib and another is a complementary recess.

In some embodiments, the diaphragm has a fixed portion and a movable portion, the movable portion being movable relative to the fixed portion between a closed position, at which the fixed portion and the movable portion are positioned across the interior airflow path, and an open position, at which the movable portion is displaced to define a bypass opening exhibiting a reduced airflow restriction passed the diaphragm.

In some embodiments, the system further comprises a first actuator slidably mounted to the housing, the first actuator having a first contact surface disposed along the interior airflow path at a distal side of the diaphragm.

In some embodiments, the first actuator is movable between an engaged position, at which the first contact surface urges a corresponding portion of the diaphragm to the open position, and a disengaged position, at which the first contact surface does not counter biasing of the diaphragm.

In some embodiments, the first actuator has a first actuation surface disposed adjacent the exterior surface of the housing.

In some embodiments, positioning of the first actuation surface repositions the first contact surface.

In some embodiments, the system further comprises a second actuator slidably mounted to the housing, the second actuator having a second contact surface disposed along the interior airflow path at the distal side of the diaphragm.

In some embodiments, the second actuator is movable between an engaged position, at which the second contact surface urges a corresponding portion of the diaphragm to the open position, and a disengaged position, at which the second contact surface does not counter biasing of the diaphragm.

In some embodiments, the system is configured such that, responsive to the first actuator being in the engaged position and the second actuator being in the engaged position, the diaphragm exhibits the open position.

In some embodiments, the system further comprises a bypass mechanism having a shaft and a bypass actuator, the shaft mounted to the housing and extending into the interior airflow path, the shaft having a first end positioned outside of the housing, the bypass actuator having a first bypass contact surface disposed along the interior airflow path at a distal side of the diaphragm.

In some embodiments, the bypass actuator is movable, in response to movement of the first end of the shaft, between a bypass position, at which the first bypass contact surface urges a corresponding portion of the diaphragm to the open position, and a non-bypass position, at which the first bypass contact surface does not counter biasing of the diaphragm.

In some embodiments, the shaft is configured to rotate about a shaft axis for moving the first bypass contact surface between the bypass position and the non-bypass position.

In some embodiments, the system further comprises a tracheostomy tube.

In some embodiments, a mount is configured to couple between the tracheostomy tube and the adjustable-flow tracheostomy valve assembly.

In some embodiments, the system further comprises at least one of a ventilator circuit, a closed suctioning system, a swivel adapter, a supplemental oxygen system, a heat and moisture exchange filter, an antibiotic coated head and moisture exchange filter, or a humidification system, operatively coupled to the adjustable-flow tracheostomy valve assembly.

Another example embodiment, among various others, is a method for adjusting airflow restriction for a user of a tracheostomy valve assembly. The method comprises: providing a tracheostomy valve assembly having a housing and a diaphragm, the housing defining an interior airflow path, the housing having an exterior surface, a distal aperture defining a distal opening extending from the exterior surface to the interior flow path, and a proximal aperture defining a proximal opening, the distal opening and the proximal opening communicating with the interior airflow path, the diaphragm being disposed within the housing along the interior airflow path between the distal opening and the proximal opening, the diaphragm being biased to a closed position to prevent air from passing the diaphragm along the interior airflow path, the diaphragm being configured to selectively move to an open position to enable air to be drawn into the distal opening, passed the diaphragm, and out of the proximal opening in an inhaling direction in response to a proximal side of the diaphragm being exposed to a predetermined negative air pressure applied at the diaphragm as a suction force; and urging the diaphragm away from the closed position with an actuation surface, movably coupled to the housing, to adjust airflow restriction through the tracheostomy valve assembly.

In some embodiments, the actuation surface is one of a plurality of actuation surfaces movably coupled to the housing.

In some embodiments, the method further comprises using each of the plurality of actuation surfaces independently to adjust the airflow restriction through the tracheostomy valve assembly.

In some embodiments, the diaphragm has a fixed portion and a movable portion, the movable portion being movable relative to the fixed portion between a closed position, at which the fixed portion and the movable portion are positioned across the interior airflow path, and an open position, at which the movable portion is displaced to define a bypass opening exhibiting a reduced airflow restriction passed the diaphragm.

In some embodiments, the urging of the diaphragm away from the closed position comprises positioning the movable portion relative to the fixed portion of the diaphragm to adjust the airflow restriction through the tracheostomy valve assembly.

Other systems, methods, features, and advantages of the present disclosure will be or may become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

As will be described in detail, the present disclosure involves tracheostomy valve assemblies that are configured to accommodate adjustable airflow rates. In some embodiments, an adjustable-flow tracheostomy valve assembly is provided that incorporates provisions for mechanically urging a diaphragm of the valve away from a closed position (such as at indexed increments), thereby enabling airflow restriction through the valve assembly to be adjusted. In some embodiments, such adjustable-flow tracheostomy valve assembly may include one or more of a flow-adjustment component with a movable wall portion, an actuator, a bypass actuator, and a segmented diaphragm.

Figure 1:
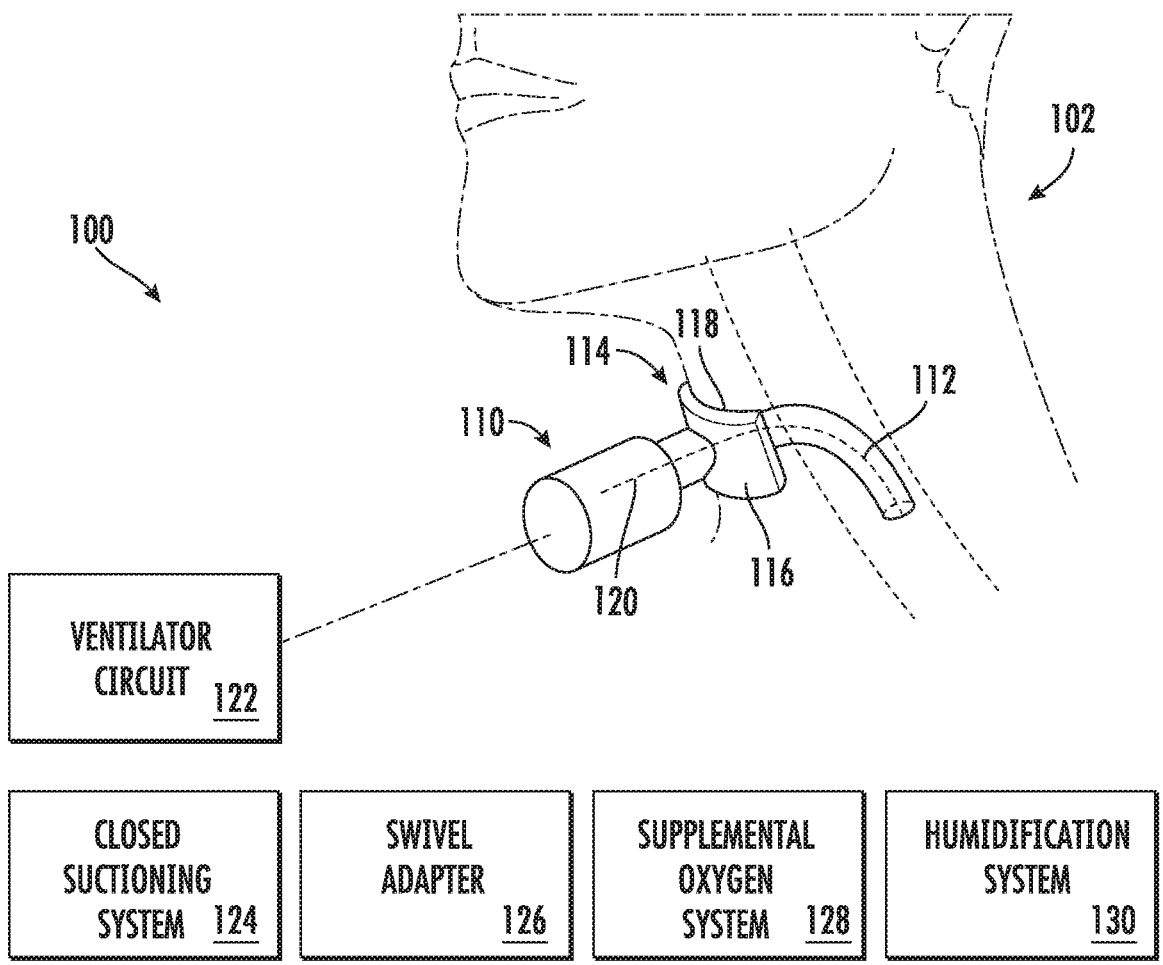
FIG. 1 is a schematic diagram of an example embodiment of a system that incorporates an adjustable-flow tracheostomy valve assembly.

In this regard, FIG. 1 is a schematic diagram of an example embodiment of a system that incorporates an adjustable-flow tracheostomy valve assembly. As shown in FIG. 1, system 100 is depicted in an installed configuration attached to a patient 102 via a stoma attributable to a tracheostomy. System 100 includes an adjustable-flow tracheostomy valve assembly 110, a tracheostomy tube 112, and a mount 114 that is configured to couple between adjustable-flow tracheostomy valve assembly 110 and tracheostomy tube 112. In the embodiment of FIG. 1, mount 114 incorporates a base plate 116 with a proximal surface 118 that is configured to be oriented toward the patient.

As shown, adjustable-flow tracheostomy valve assembly 110, mount 114, and tracheostomy tube 112 provide an airflow path 120 for the patient. Optionally, system 100 may include one or more of various components and/or systems operatively coupled to the adjustable-flow tracheostomy valve assembly, such as a ventilator circuit 122, a closed suctioning system 124, a swivel adapter 126, a supplemental oxygen system 128, and a humidification system 130, among others, such as a heat and moisture exchange filter and an antibiotic coated head and moisture exchange filter, for example.

Figure 2:
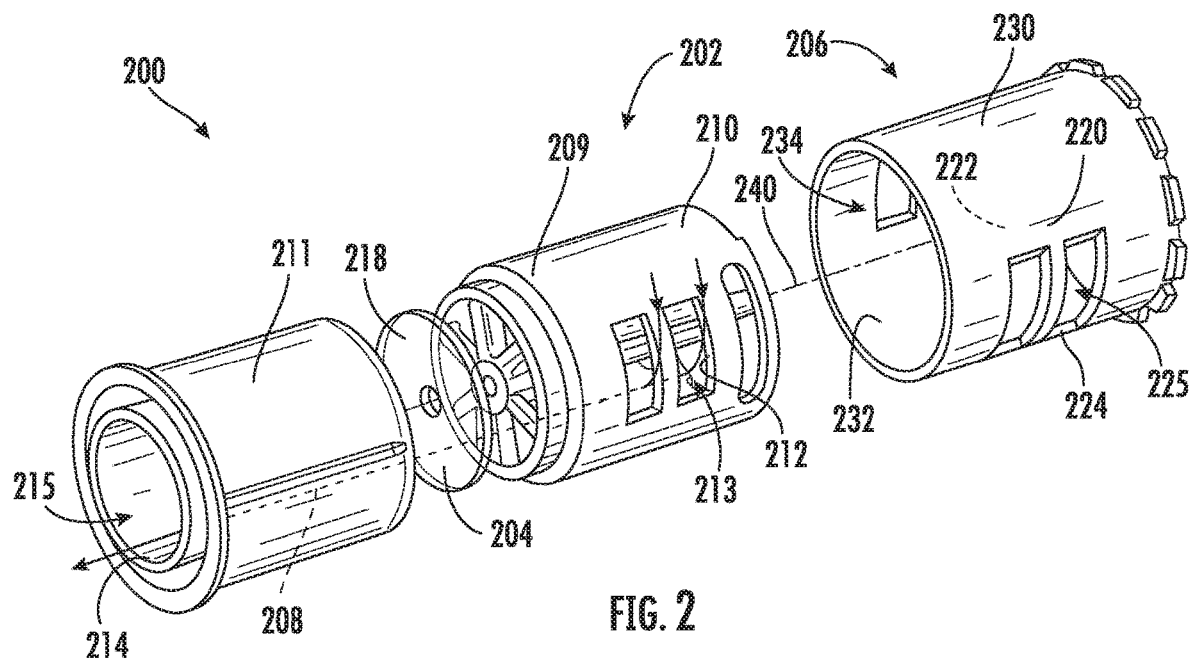
FIGS. 2 and 3 are partially-exploded, schematic diagrams of an example embodiment of an adjustable-flow tracheostomy valve assembly.
Figure 3:
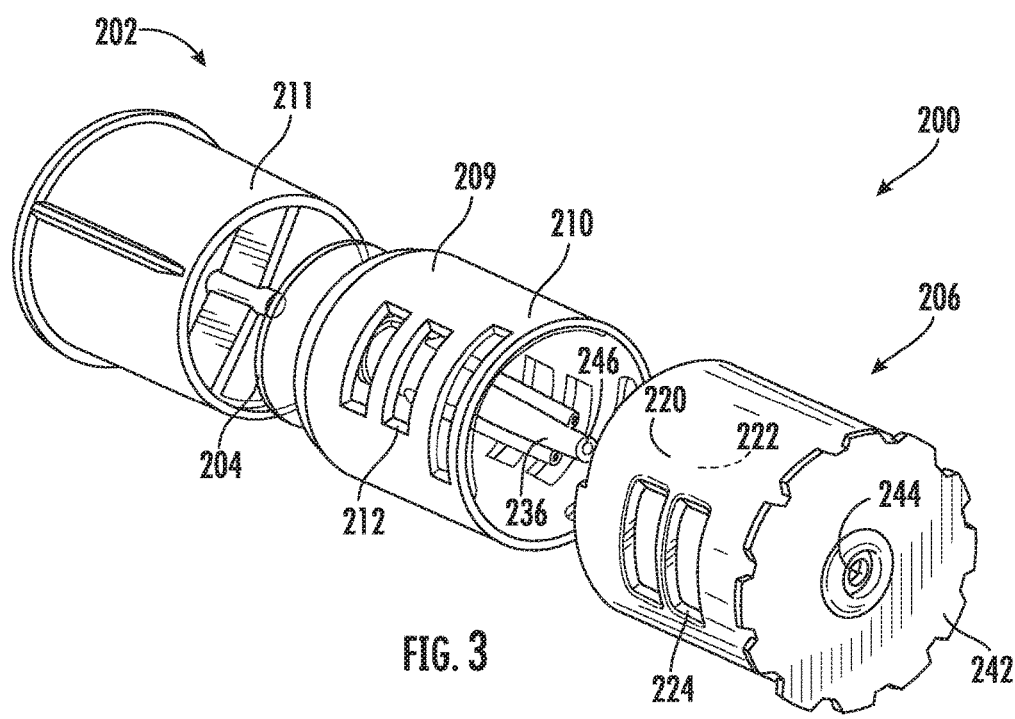

FIGS. 2 and 3 are partially-exploded, schematic diagrams of an example embodiment of an adjustable-flow tracheostomy valve assembly 200. It should be noted that the orientation of adjustable-flow tracheostomy valve assembly 200 in these figures is rotated 180 degrees compared to the orientation of the valve assembly depicted in FIG. 1.

As shown in FIGS. 2 and 3, adjustable-flow tracheostomy valve assembly 200 incorporates a housing 202, a diaphragm 204 (e.g., a silicone diaphragm), and a flow-adjustment component 206. Housing 202 defines an interior airflow path 208 and includes an exterior surface 210. Housing 202 also includes a distal portion 209 with a distal aperture 212 and a proximal portion 211 with a proximal aperture 214. Distal aperture 212 defines a distal opening 213 that extends from exterior surface 210 to interior airflow path 208. Proximal aperture 214 defines a proximal opening 215. Notably, both distal opening 213 and proximal opening 215 communicate with interior airflow path 208. In some embodiments, hosing 202 may be formed of a conventional tracheostomy valve assembly, such as a Passy-Muir Speaking Valve, for example.

Diaphragm 204 is disposed within housing 202 along interior airflow path 208 between distal opening 213 and proximal opening 215. Diaphragm 204 is biased to a closed position to prevent air from passing diaphragm 204 along interior airflow path 208. In particular, diaphragm 204 is configured to selectively move to an open position to enable air to be drawn into distal opening 213, passed diaphragm 204, and out of proximal opening 215 in an inhaling direction in response to a proximal side 218 of diaphragm 204 being exposed to a predetermined negative air pressure applied at diaphragm 204 as a suction force.

Flow-adjustment component 206 includes a wall portion 220 with an inner surface 222 that is configured to conform to exterior surface 210 of the housing at least to the extent required to prevent airflow through distal opening 213 when in a closed position. In this regard, wall portion 220 includes a flow-adjustment aperture 224 defining a flow-adjustment opening 225. Wall portion 220 is movable relative to housing 202 between an open position (shown in FIG. 6), at which wall portion 220 does not obstruct airflow through distal opening 213, and a closed position (shown in FIG. 4), at which wall portion 220 prevents air from passing through flow-adjustment opening 225 and into distal opening 213 owing to misalignment of the openings. Notably, flow-adjustment opening 225 may be of a size that is larger than that of distal opening 213 so that airflow is not restricted when the openings are aligned (i.e., in the open position).

It should be noted that, in the embodiment of FIGS. 2 and 3, flow-adjustment component 206 includes opposing pairs of flow-adjustment openings that are positioned to align with corresponding pairs of distal openings of housing 202. Different numbers, orientations, and/or configurations of such openings may be used in different embodiments.

Referring back to FIGS. 2 and 3, flow-adjustment component 206 includes a sidewall 230, an inner surface 232 of which defines a receptacle 234. Receptacle 234 is configured to receive a distal end 236 of housing 202 so that distal opening 213 may be positioned within receptacle 234. Notably, wall portion 220 is a portion of sidewall 230, which in this embodiment is cylindrical.

In operation, wall portion 220 is configured to move with flow-adjustment component 206. In this embodiment, wall portion 220 is rotatable relative to housing 202. In some embodiments, this is facilitated by a hub 236 that extends along a central axis 240 of adjustable-flow tracheostomy valve assembly 200. Specifically, flow-adjustment component 206 includes an end cap 242 with a central aperture 244, within which an end 246 of hub 236 seats to facilitate a rotational coupling.

Figure 4:
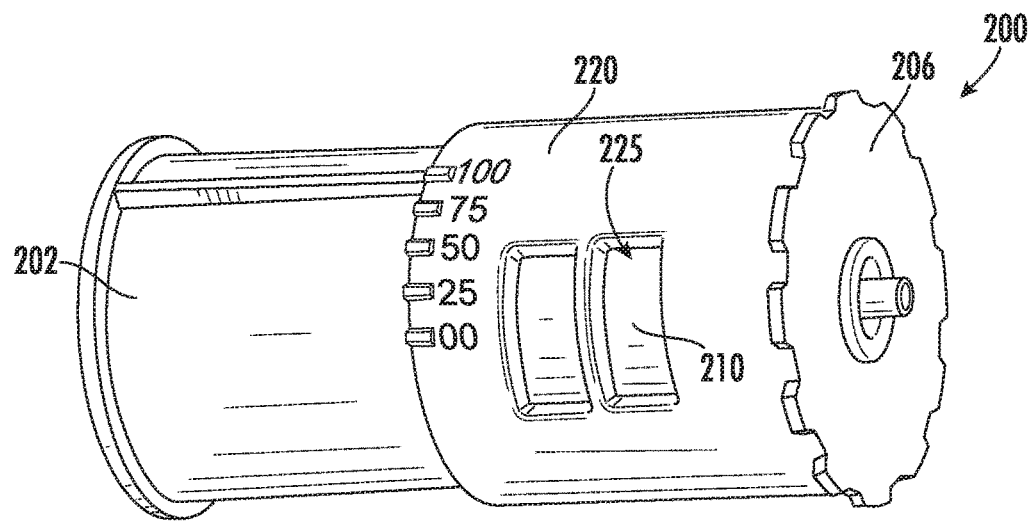
FIGS. 4-6 are schematic diagrams of an example embodiment of an adjustable-flow tracheostomy valve assembly showing various positions.
Figure 5:
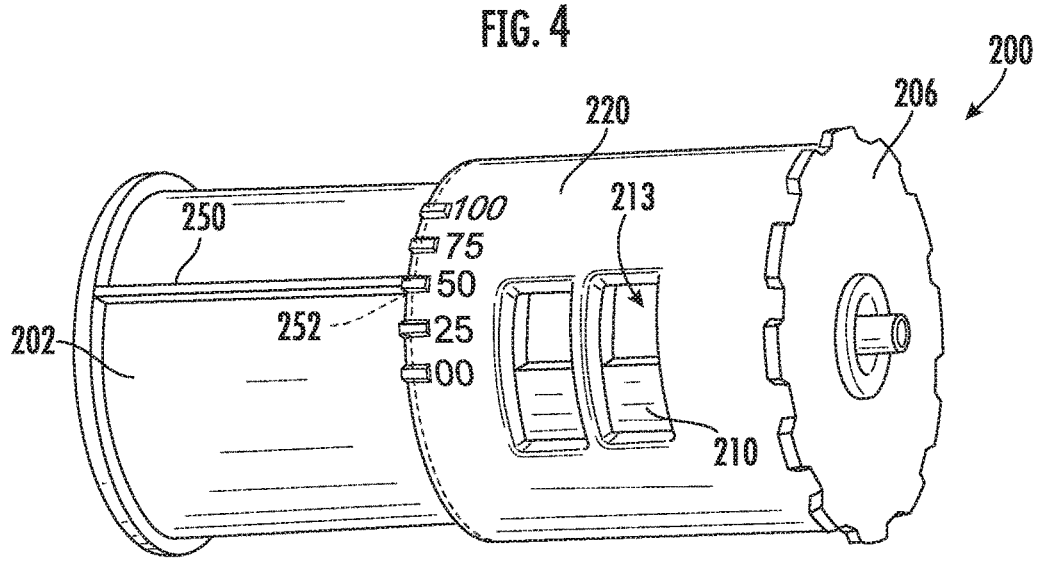
Figure 6:
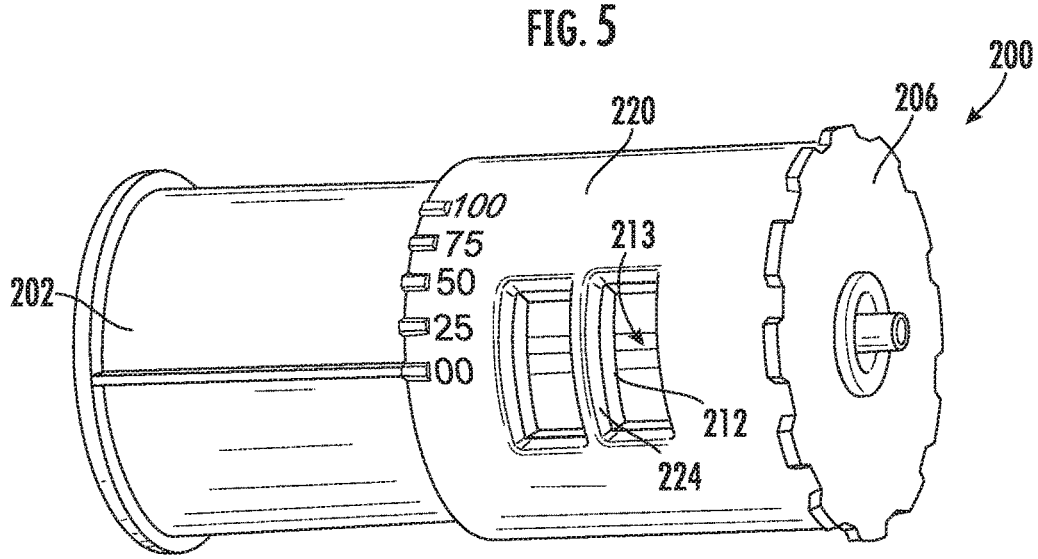

FIGS. 4-6 are schematic diagrams of adjustable-flow tracheostomy valve assembly 200 showing various adjustments to airflow restriction. In particular, FIG. 4 depicts the closed position at which wall portion 220 prevents air from passing through flow-adjustment opening 225 and into distal opening 213. This is due to misalignment of the openings 225/213. In contrast, the open position is depicted in FIG. 6 at which wall portion 220 does not obstruct airflow through distal opening 213. In particular, flow-adjustment opening 225 is aligned with distal opening 213. In this embodiment, these positions are set by engagement between a mating feature 250 disposed on inner surface 232 of the flow-adjustment component 206 and a corresponding mating feature 252 at exterior surface 210 of housing 202. In some embodiments, mating feature 250 and corresponding mating feature 252 are configured as a protruding rib and a complementary recess, respectively (as shown in FIG. 5). Notably, in other embodiments, the positions of the mating features may be transposed.

In some embodiments, such as shown in FIG. 5, flow-adjustment component 206 and housing 202 are configured to exhibit at least a first indexed position, which is an intermediate position between the open position and the closed position. As in the depicted embodiment, each of the positions may be identified by an indicator that identifies the extent to which airflow restriction through the assembly is being adjusted. In this embodiment, three intermediate indexed positions are provided via corresponding mating features to offer a range of positions from 0% and 100% airflow restriction.

Figure 7:
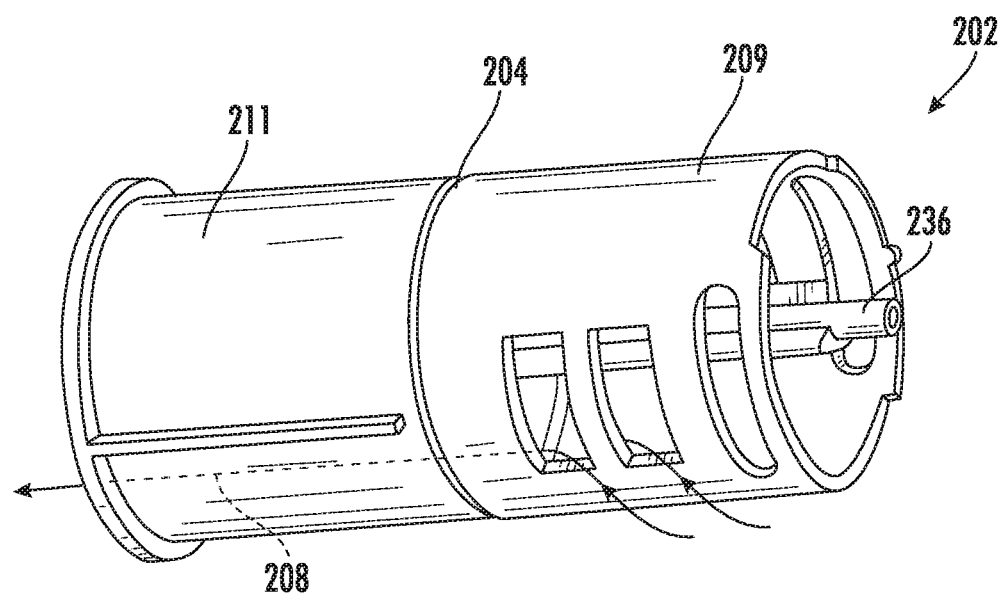
FIGS. 7 and 8 are schematic diagrams of an example embodiment of an adjustable-flow tracheostomy valve assembly showing various assembly details.
Figure 8:
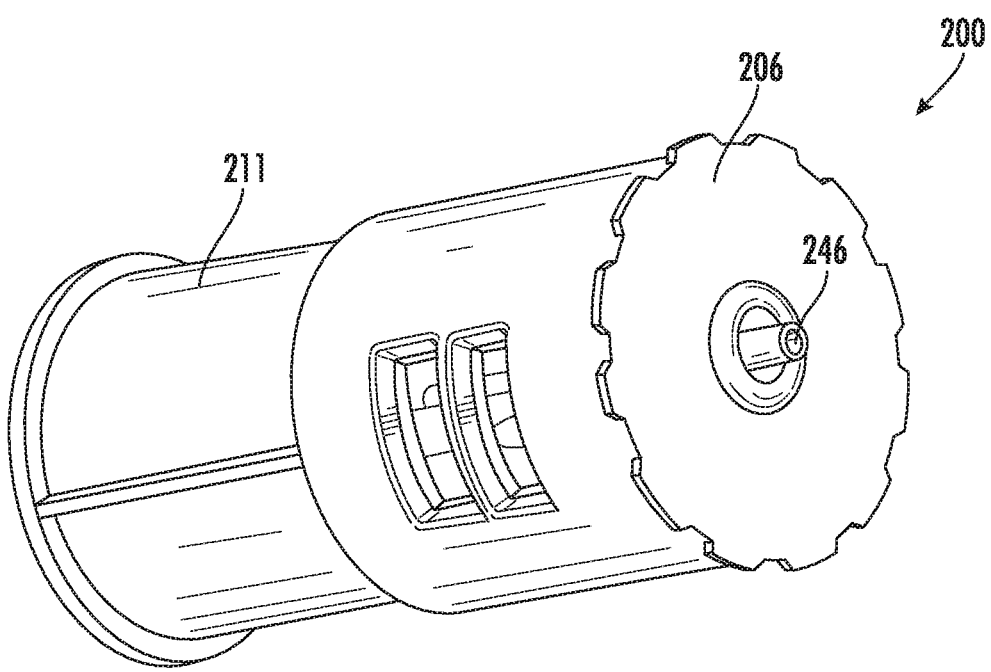

FIGS. 7 and 8 are schematic diagrams of adjustable-flow tracheostomy valve assembly 200 showing various assembly details. By way of example, diaphragm 204 is disposed along interior airflow path 208 between a proximal portion 211 and a distal portion 209 of housing 202. Diaphragm 204 may be secured in place in various manners, such as by adhesive bonding or ultrasonic welding, for example. Flow-adjustment component 206 may be rotatably mounted to housing 202 such as by hot melting end 246 of hub 236 to form an interference fit.

Figure 9A:
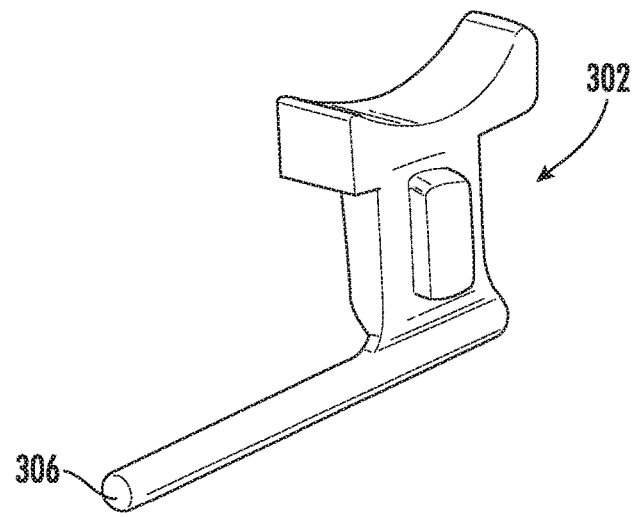
FIG. 9A is a schematic diagram of an example embodiment of an actuator.
Figure 9B:
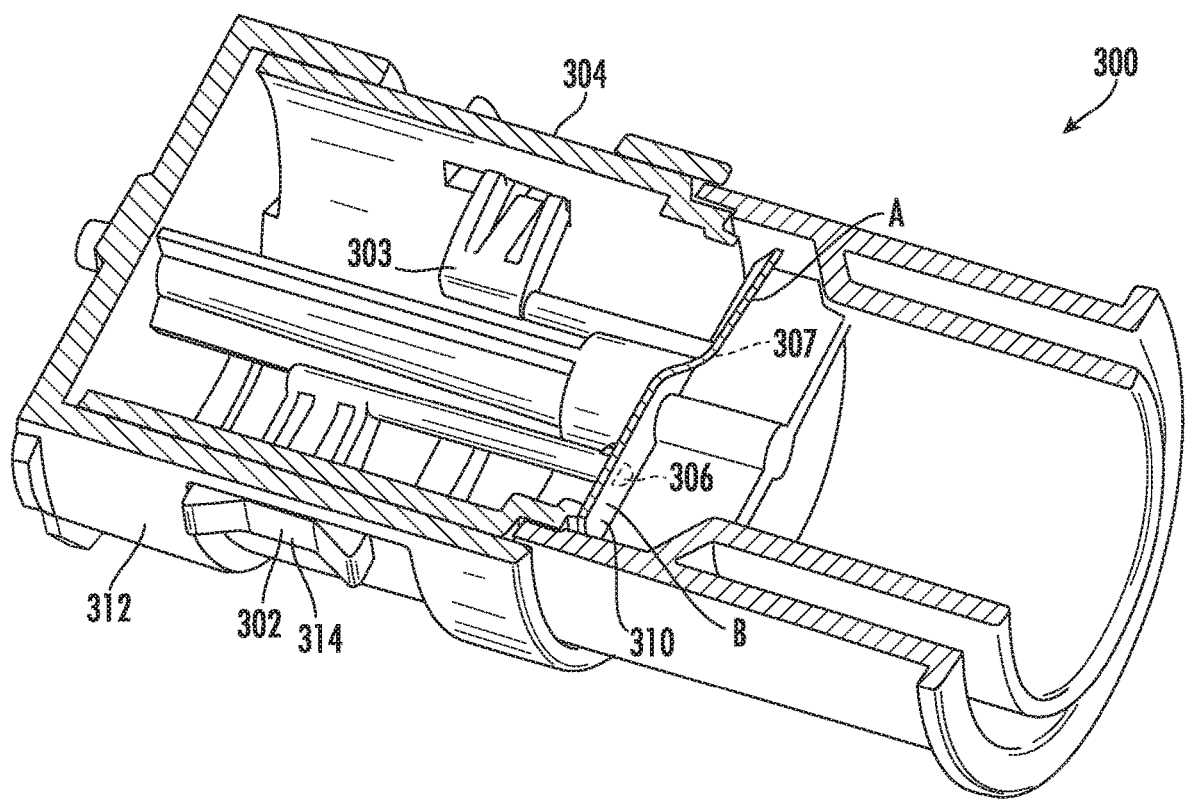
FIG. 9B is a cut-away view of an example embodiment of an adjustable-flow tracheostomy valve assembly incorporating two actuators.

FIG. 9A is a schematic diagram depicting an embodiment of an actuator 302 with a contact surface 306. As shown in FIG. 9B, actuator 302 is incorporated into an adjustable-flow tracheostomy valve assembly 300. Adjustable-flow tracheostomy valve assembly 300 also incorporates a second actuator 303 with a corresponding contact surface 307. Each of the actuators slidably mounts to the distal portion of housing 304; in this embodiment, at opposing sides of the housing. Retention of each of the actuators to the housing is provided by interference fits.

In operation, each of the actuators is independently movable so that the actuator and associated contact surface can be selectively positioned between an engaged position, at which contact surface urges a corresponding portion of diaphragm 310 to the open position (depicted by contact surface 307 at position A), and a disengaged position, at which the contact surface does not counter biasing of the diaphragm (depicted by contact surface 306 at position B). As another example, responsive to both actuators being in the engaged position, diaphragm 310 exhibits a full-open position (not shown).

For facilitating movement of an actuator, each includes an actuation surface disposed adjacent the exterior surface 312 of housing 304. By way of example, actuator 302 incorporates an actuation surface 314. Positioning of the respective actuation surface repositions the corresponding contact surface.

Figure 10:
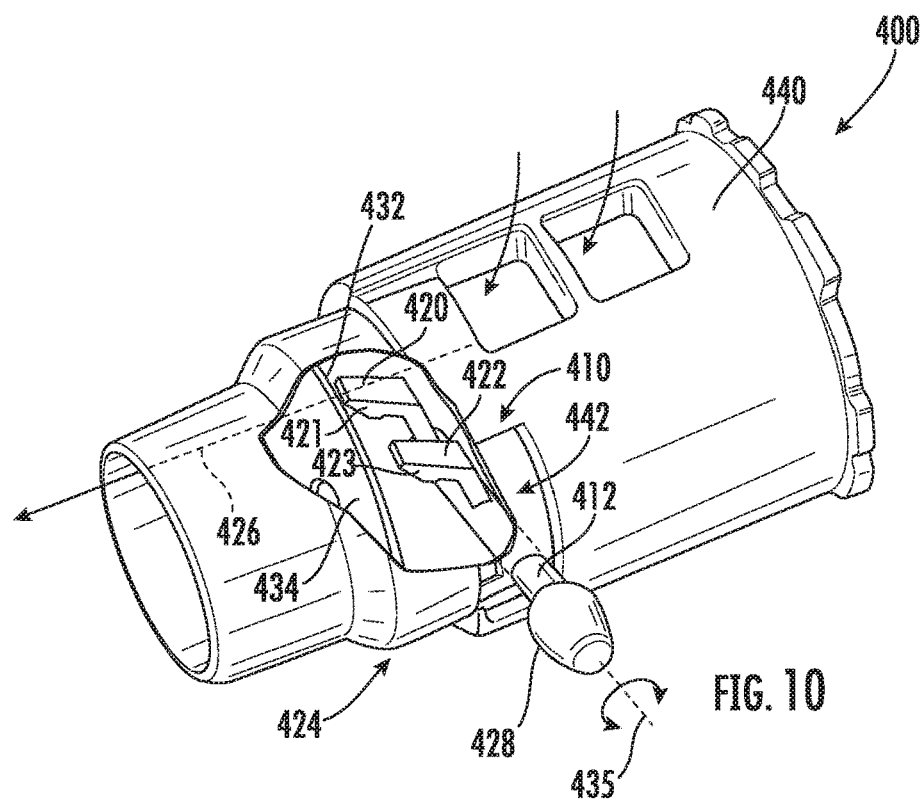
FIGS. 10 and 11 are schematic diagrams of another example embodiment of an adjustable-flow tracheostomy valve assembly showing detail of an example embodiment of a bypass actuator.
Figure 11:
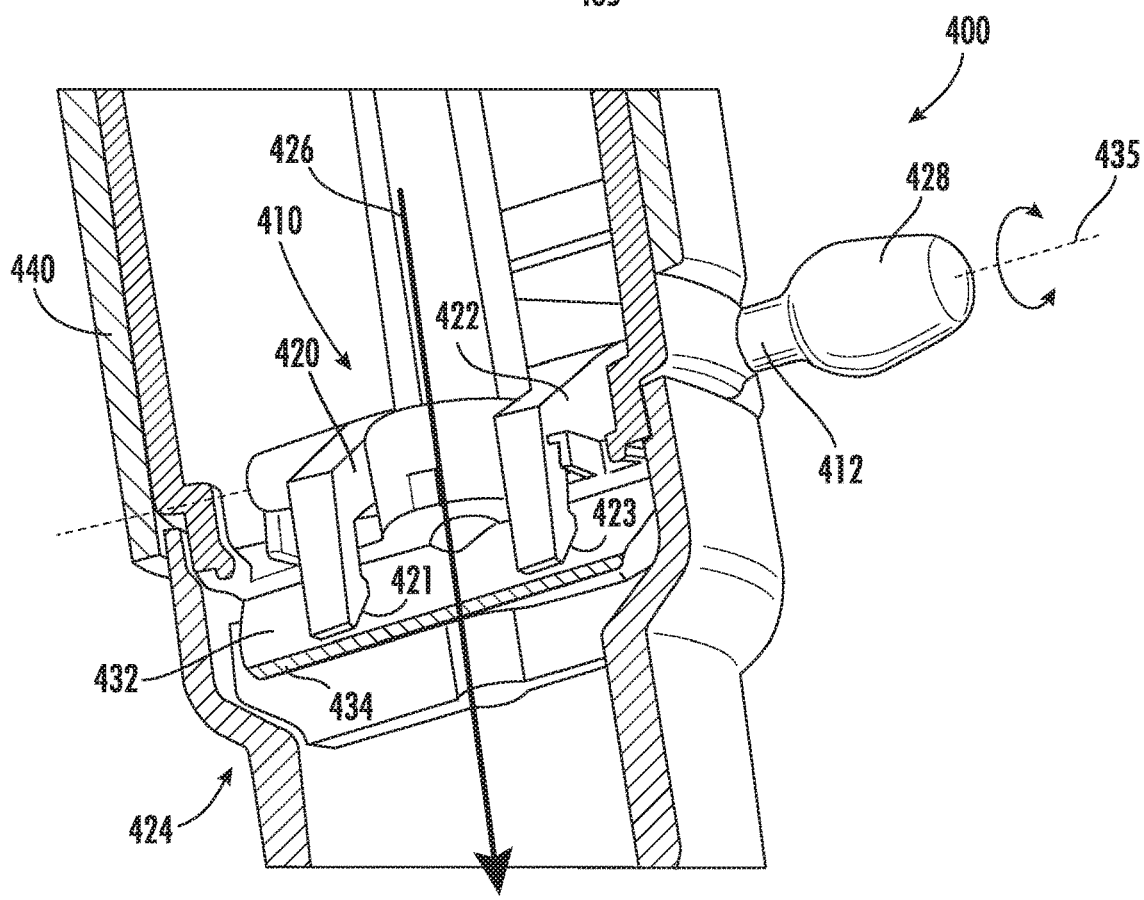

FIGS. 10 and 11 are schematic diagrams of another example embodiment of an adjustable-flow tracheostomy valve assembly 400. As shown, adjustable-flow tracheostomy valve assembly 400 incorporates a bypass mechanism 410 that includes a shaft 412 and a pair of bypass actuators 420/422. It should be noted that, in other embodiments, a different number of bypass actuators may be used.

Shaft 412 is rotatably mounted to housing 424 and extends into interior airflow path 426. Shaft 412 includes a first end 428, which is positioned outside of housing 424 and is configured for being moved by a user. Each bypass actuator includes a bypass contact surface disposed along interior airflow path 426 at a distal side 432 of an associated diaphragm 434. Specifically, bypass actuator 420 includes a bypass contact surface 421 and bypass actuator 422 includes a bypass contact surface 423.

Each bypass actuator is carried by shaft 412 and, thus, is movable in response to movement of first end 428 of the shaft, which is configured to rotate about a shaft axis 435. In particular, each bypass actuator is movable between a bypass position (depicted in FIG. 11), at which each of the bypass contact surfaces urges a corresponding portion of diaphragm 434 to the open position, and a non-bypass position (depicted in FIG. 10), at which each of the bypass contact surfaces does not counter biasing of the diaphragm.

Also depicted in FIG. 10 is flow-adjustment component 440, which incorporates a cutout portion 442 for facilitating rotation of flow-adjustment component 440 about housing 424 without impinging upon shaft 412.

Figure 12:
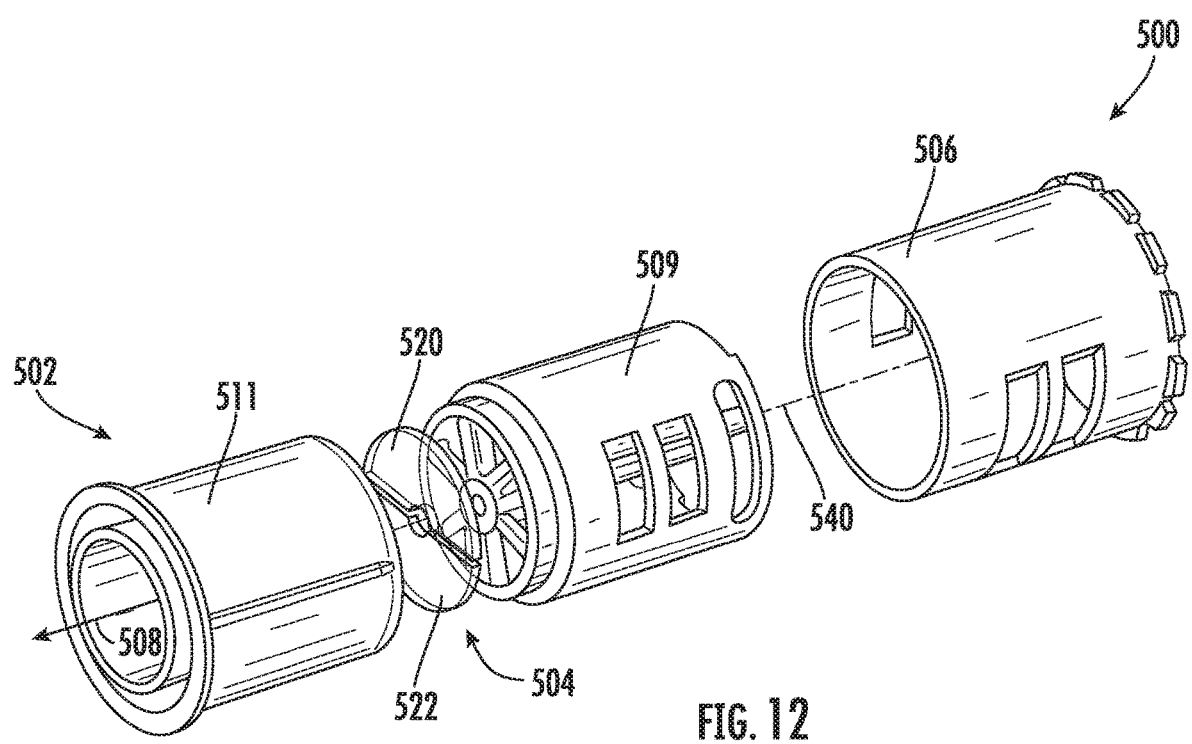
FIG. 12 is a partially-exploded, schematic diagram of another example embodiment of an adjustable-flow tracheostomy valve assembly.

FIG. 12 is a partially-exploded, schematic diagram of another example embodiment of an adjustable-flow tracheostomy valve assembly. As shown in FIG. 12, adjustable-flow tracheostomy valve assembly 500 incorporates a housing 502, a diaphragm 504, and a flow-adjustment component 506. Housing 502 defines an interior airflow path 508 and includes a distal portion 509 and a proximal portion 511. Diaphragm 504 is disposed within housing 502 along interior airflow path 508 and is biased to a closed position to prevent air from passing diaphragm 504 along interior airflow path 508. As described with respect to other embodiments, diaphragm 504 is configured to selectively move to an open position to enable air to be drawn into housing 502 and passed diaphragm 504 in an inhaling direction in response to a proximal side of the diaphragm being exposed to a predetermined negative air pressure applied as a suction force. However, unlike the other embodiments, diaphragm 504 exhibits a segmented configuration.

Figure 13A:
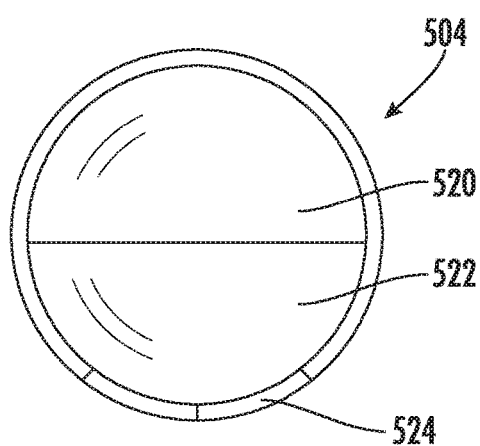
FIGS. 13A-13D are schematic diagrams of an example embodiment of an adjustable diaphragm.
Figure 13B:
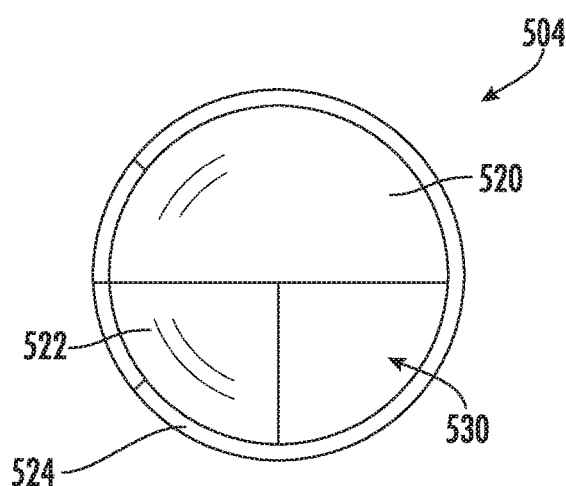
Figure 13C:
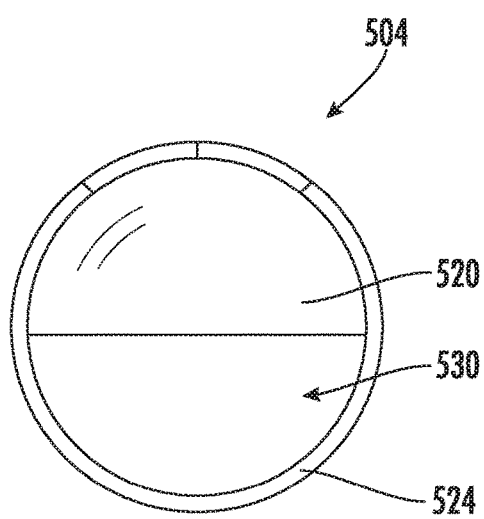
Figure 13D:
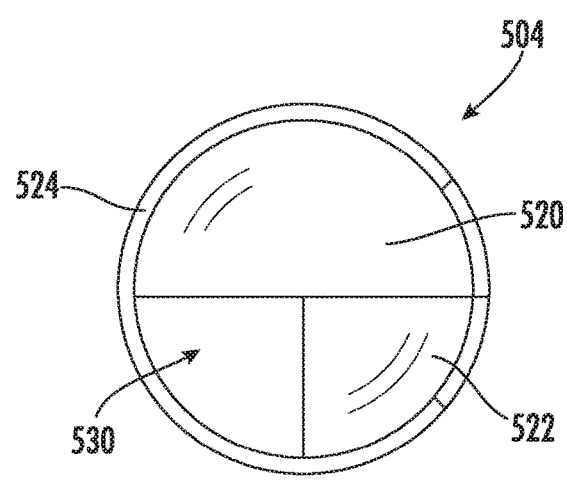

In this regard (and with reference to FIGS. 13A-13D), diaphragm 504 incorporates a fixed portion 520 and a movable portion 522. Movable portion 522 is movable relative to fixed portion 520 between a closed position (see FIGS. 12 and 13A), at which fixed portion 520 and movable portion 522 are positioned across interior airflow path 508, and an open position (see FIG. 13C), at which movable portion 522 is displaced to define a bypass opening 530 exhibiting a reduced airflow restriction passed the diaphragm.

In some embodiments, movement of portion 522 is associated with rotation of movable portion 522 about an axis 540 (e.g., a central axis). Specifically, in some embodiments, movable portion 522 is mounted to an actuator surface that is configured as a mounting frame 524 to which the movable portion is mounted. In such an embodiment, rotation of flow-adjustment component 506 about housing 502 causes mounting frame 524 and movable portion 522 to rotate relative to housing 502 and fixed portion 520, which is fixed in position relative to the housing.

FIGS. 13A-13D show various positions of diaphragm 504 as movable portion 522 is rotated one quarter revolution clockwise between each view. Various positions of movable portion 522 (other than those shown) may be provided to alter the size of bypass opening 530 in other embodiments.

In other embodiments, various configurations of diaphragm portions may be used. By way of example, multiple movable portions and/or multiple fixed portions may be used. For instance, the portions may be configured as quarter portions of which one may be fixed and three may be movable. So configured, rotation of the flow-adjustment component about the housing causes corresponding mounting frames to which the movable portions are mounted to rotate relative to the housing and the fixed portion. Continued rotation may result in successive 25% increments in diaphragm closure as each movable portion is moved to its extended (airflow path-blocking) position. Thus, in such an embodiment, 25, 50, 75 and 100% incremental closures may be achieved as desired based on positioning of the actuator surfaces.

Figure 14:
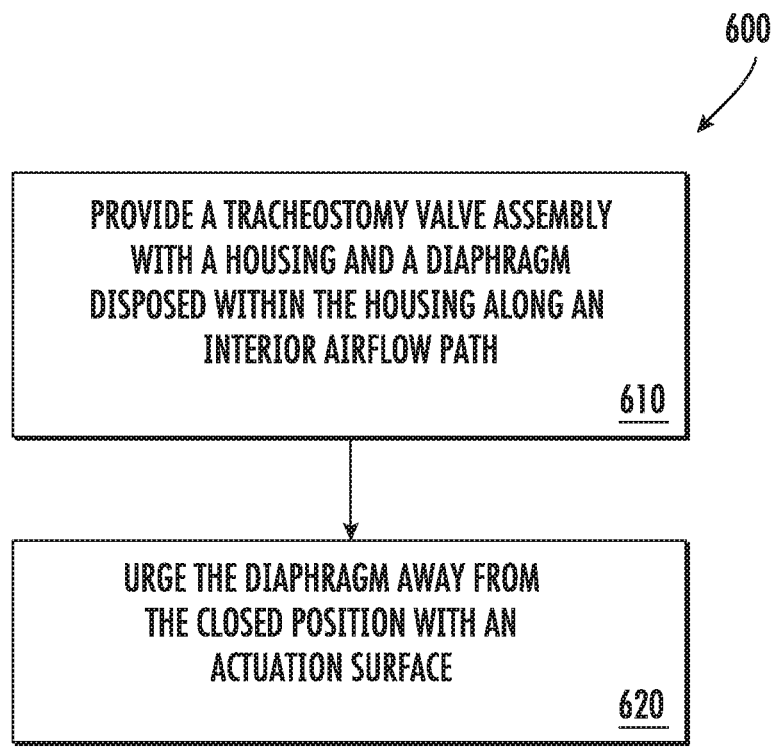
FIG. 14 is a flowchart depicting functionality of another example embodiment.

FIG. 14 is a flowchart depicting functionality (or method) associated with another example embodiment. In particular, an example embodiment of a method for adjusting airflow restriction for a user of a tracheostomy valve assembly is provided. As shown in FIG. 14, method 600 may be construed as beginning at block 610, in which a tracheostomy valve assembly is provided. In some embodiments, the tracheostomy valve assembly incorporates a housing and a diaphragm. Such a housing defines an interior airflow path. The housing also includes an exterior surface, a distal aperture defining a distal opening extending from the exterior surface to the interior flow path, and a proximal aperture defining a proximal opening. The distal opening and the proximal opening communicate with the interior airflow path. The diaphragm is disposed within the housing along the interior airflow path between the distal opening and the proximal opening. The diaphragm also is biased to a closed position to prevent air from passing the diaphragm along the interior airflow path, and is configured to selectively move to an open position to enable air to be drawn into the distal opening, passed the diaphragm, and out of the proximal opening in an inhaling direction in response to a proximal side of the diaphragm being exposed to a predetermined negative air pressure applied at the diaphragm as a suction force.

In block 620, an actuation surface, which is movably coupled to the housing, is used to urge (e.g., mechanically urge) the diaphragm away from the closed position to adjust airflow restriction through the tracheostomy valve assembly. In some embodiments, the urging of the diaphragm causes at least a portion of the diaphragm to deflect. In some embodiments, the actuation surface is one of a plurality of actuation surfaces movably coupled to the housing. In some of these embodiments, each of the plurality of actuation surfaces is used independently to adjust the airflow restriction through the tracheostomy valve assembly. By way of example, an actuation surface may be a contact surface of an actuator (e.g., a bypass contact surface of a bypass actuator).

In some embodiments, the diaphragm incorporates a fixed portion and a movable portion, in which case, the method involves controlling the percentage closure of the diaphragm by positioning the movable portion of the diaphragm to adjust the airflow restriction through the tracheostomy valve assembly. In these embodiments, the urging of the diaphragm includes displacement of at least the movable portion of the diaphragm relative to a fixed portion. In such an embodiment, the actuation surface may be associated with one or more components used in moving the movable portion, such as a mounting frame to which the movable portion is mounted.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A system comprising:
   an adjustable-flow tracheostomy valve assembly having a housing, a diaphragm, and a flow-adjustment component;
   the housing defining an interior airflow path, the housing having an exterior surface, a distal aperture defining a distal opening extending from the exterior surface to the interior airflow path, and a proximal aperture defining a proximal opening, the distal opening and the proximal opening communicating with the interior airflow path;
   the diaphragm being disposed within the housing along the interior airflow path between the distal opening and the proximal opening, the diaphragm being biased to a closed position to prevent air from passing the diaphragm along the interior airflow path, the diaphragm being configured to selectively move to an open position to enable air to be drawn into the distal opening, past the diaphragm, and out of the proximal opening in an inhaling direction in response to a proximal side of the diaphragm being exposed to a predetermined negative air pressure applied at the diaphragm as a suction force;
   the flow-adjustment component having a wall portion with an inner surface configured to conform to the exterior surface of the housing, the wall portion further having a flow-adjustment aperture defining a flow-adjustment opening, the wall portion being movable relative to the housing between an open position, at which the wall portion does not obstruct airflow through the distal opening, and a closed position, at which the wall portion prevents air from passing through the flow-adjustment opening and into the distal opening;
   a bypass mechanism having a shaft and a bypass actuator, the shaft mounted to the housing and extending into the interior airflow path, the shaft having a first end positioned outside of the housing, the bypass actuator having a first bypass contact surface disposed along the interior airflow path at a distal side of the diaphragm; and
   the bypass actuator is movable, in response to movement of the first end of the shaft, between a bypass position, at which the first bypass contact surface urges a corresponding portion of the diaphragm to the open position, and a non-bypass position, at which the first bypass contact surface does not counter biasing of the diaphragm.

2. The system of claim 1, wherein the wall portion is configured to move with an entirety of the flow-adjustment component.

3. The system of claim 1, wherein:
   the flow-adjustment component has a sidewall, an inner surface of which defines a receptacle, which is configured to receive therein a distal end of the housing such that the distal opening is positioned within the receptacle; and
   the wall portion is a portion of the sidewall.

4. The system of claim 3, wherein:
   the sidewall of the flow-adjustment component is cylindrical; and
   the wall portion is rotatable relative to the housing.

5. The system of claim 1, wherein the flow-adjustment component and the housing are configured to exhibit a first indexed position between the open position and the closed position.

6. The system of claim 5, wherein engagement between a mating feature disposed on an inner surface of the flow-adjustment component and a corresponding mating feature of the exterior surface of the housing set the first indexed position.

7. The system of claim 6, wherein, of the mating feature and the corresponding mating feature, one is a protruding rib and another is a complementary recess.

8. The system of claim 1, wherein the diaphragm has a fixed portion and a movable portion, the movable portion being movable relative to the fixed portion between a closed position, at which the fixed portion and the movable portion are positioned across the interior airflow path, and an open position, at which the movable portion is displaced to define a bypass opening exhibiting a reduced airflow restriction passed the diaphragm.

9. The system of claim 1, wherein
   the first bypass actuator is slidably mounted to the housing.

10. The system of claim 9, wherein:
    the first bypass actuator has a first actuation surface disposed adjacent the exterior surface of the housing;
    wherein positioning of the first actuation surface repositions the first bypass contact surface.

11. The system of claim 9, wherein:
    the system further comprises a second bypass actuator slidably mounted to the housing, the second bypass actuator having a second bypass contact surface disposed along the interior airflow path at the distal side of the diaphragm;
    the second bypass actuator is movable between a bypass position at which the second bypass contact surface urges a corresponding portion of the diaphragm to the open position, and a non-bypass position, at which the second bypass contact surface does not counter biasing of the diaphragm.

12. The system of claim 11, wherein the system is configured such that, responsive to the first bypass actuator being in the bypass position and the second bypass actuator being in the bypass position, the diaphragm exhibits the open position.

13. The system of claim 1, wherein the shaft is configured to rotate about a shaft axis for moving the first bypass contact surface between the bypass position and the non-bypass position.

14. The system of claim 1, wherein
the diaphragm has a fixed portion and a movable portion, the movable portion being movable relative to the fixed portion between a closed position, at which the fixed portion and the movable portion are positioned across the interior airflow path, and an open position, at which the movable portion is displaced to define a bypass opening exhibiting a reduced airflow restriction past the diaphragm.

15. The system of claim 1, further comprising:
a tracheostomy tube; and
a mount configured to couple between the tracheostomy tube and the adjustable-flow tracheostomy valve assembly.

16. The system of claim 1, further comprising at least one of a ventilator circuit, a closed suctioning system, a swivel adapter, a supplemental oxygen system, or a humidification system, operatively coupled to the adjustable-flow tracheostomy valve assembly.

17. A method for adjusting airflow restriction for a user of a tracheostomy valve assembly, the method comprising:
providing a tracheostomy valve assembly having a housing and a diaphragm, the housing defining an interior airflow path, the housing having an exterior surface, a distal aperture defining a distal opening extending from the exterior surface to the interior flow path, and a proximal aperture defining a proximal opening, the distal opening and the proximal opening communicating with the interior airflow path, the diaphragm being disposed within the housing along the interior airflow path between the distal opening and the proximal opening, the diaphragm being biased to a closed position to prevent air from passing the diaphragm along the interior airflow path, the diaphragm being configured to selectively move to an open position to enable air to be drawn into the distal opening, past the diaphragm, and out of the proximal opening in an inhaling direction in response to a proximal side of the diaphragm being exposed to a predetermined negative air pressure applied at the diaphragm as a suction force;
urging the diaphragm away from the closed position with an actuation surface, movably coupled to the housing, to adjust airflow restriction through the tracheostomy valve assembly;
the actuation surface is one of a plurality of actuation surfaces movably coupled to the housing; and
the method further comprises using each of the plurality of actuation surfaces independently to adjust the airflow restriction through the tracheostomy valve assembly.

18. The method of claim 17, wherein:
the diaphragm has a fixed portion and a movable portion, the movable portion being movable relative to the fixed portion between a closed position, at which the fixed portion and the movable portion are positioned across the interior airflow path, and an open position, at which the movable portion is displaced to define a bypass opening exhibiting a reduced airflow restriction past the diaphragm; and
the urging of the diaphragm away from the closed position comprises positioning the movable portion relative to the fixed portion of the diaphragm to adjust the airflow restriction through the tracheostomy valve assembly.

* * * * *